US009640373B2

(12) United States Patent
Yamaguchi

(10) Patent No.: US 9,640,373 B2
(45) Date of Patent: May 2, 2017

(54) METHOD AND SYSTEM FOR PROCESSING ANALYSIS DATA

(75) Inventor: Shinichi Yamaguchi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 601 days.

(21) Appl. No.: 14/129,718

(22) PCT Filed: Jun. 29, 2011

(86) PCT No.: PCT/JP2011/064872
§ 371 (c)(1),
(2), (4) Date: Dec. 27, 2013

(87) PCT Pub. No.: WO2013/001618
PCT Pub. Date: Jan. 3, 2013

(65) Prior Publication Data
US 2014/0156203 A1    Jun. 5, 2014

(51) Int. Cl.
G01N 31/00        (2006.01)
H01J 49/00        (2006.01)
G01N 30/86        (2006.01)
G01N 33/00        (2006.01)
G06F 19/00        (2011.01)
(Continued)

(52) U.S. Cl.
CPC ...... H01J 49/0027 (2013.01); G01N 30/8655 (2013.01); G01N 33/0004 (2013.01); G06F 19/703 (2013.01); G01N 30/72 (2013.01); G06F 19/24 (2013.01)

(58) Field of Classification Search
CPC ........... H04N 5/23206; H04N 5/23229; H04N 5/23238; H04N 5/2354; H04N 5/7491; H04N 7/106; H04N 7/18; H04N 7/181; B64C 39/024; B64C 2201/143;
(Continued)

(56) References Cited

U.S. PATENT DOCUMENTS

2007/0211928 A1*  9/2007  Weng ............... G01N 30/8624
                                              382/128
2009/0020693 A1   1/2009  Yamaguchi
(Continued)

FOREIGN PATENT DOCUMENTS

JP    2007-240374      9/2007
JP    2009-025056 A    2/2009
WO    03/102543        12/2003

OTHER PUBLICATIONS

Jun Yonekubo et al., "Feature of newest Time of Flight Mass Spectrometer LCT Premier and Applied for Food Metabolome," Chromatography, 2006, pp. 85-89, vol. 27, No. 2.
(Continued)

*Primary Examiner* — Roy Y Yi
(74) *Attorney, Agent, or Firm* — Sughrue Mion, PLLC

(57) ABSTRACT

Data of a plurality of samples collected by an LC/MS, GC/MS or other systems are converted into a two-dimensional table format. After LC/MS measurement data on a plurality of samples are obtained and the respective extracted ion chromatograms (XICs) are created, a time-axis adjustment for correcting a discrepancy in the retention time is performed, followed by a process of correcting the missing of data which has occurred in the head and/or tail section of the data as a result of the time-axis adjustment.

12 Claims, 5 Drawing Sheets

(51) Int. Cl.
*G01N 30/72* (2006.01)
*G06F 19/24* (2011.01)

(58) Field of Classification Search
CPC .......... B64C 2201/146; B64C 2201/00; B64C 2201/08; G01N 2035/0032
See application file for complete search history.

(56) References Cited

U.S. PATENT DOCUMENTS

| | | | | |
|---|---|---|---|---|
| 2010/0084552 | A1* | 4/2010 | Kawana | H01J 49/0077 250/288 |
| 2011/0184658 | A1* | 7/2011 | Maruyama | G01N 30/82 702/25 |

OTHER PUBLICATIONS

Tim P. Sangster et al., "Investigation of analytical variation in metabonomic analysis using liquid chromatography/mass spectrometry," Rapid Communications in Mass Spectrometry, 2007, pp. 2965-2970, vol. 21, No. 18.

Li Xiayan et al., "Advances in separation science applied to metabonomics," Electrophoresis, 2008, pp. 3724-3736, vol. 29, No. 18.

International Search Report of PCT/JP2011/064872 dated Aug. 23, 2011.

Communication dated Mar. 8, 2016 from the State Intellectual Property Office of the P.R.C. in counterpart Application No. 201180071984.7.

European Search Report issued Feb. 25, 2015 in European Patent Application No. 11868575.9.

Chinese Office Action issued Feb. 13, 2015 in Chinese Patent Application No. 201180071984.7.

Chinese Office Action issued Sep. 23, 2015 in Chinese Patent Application No. 201180071984.7.

Smith, Colin A. et al. XCMS: Processing Mass Spectrometry Data for Metabolite Profiling Using Nonlinear Peak Alignment, Matching, and Identification. Analytical Chemistry, vol. 78, No. 3, pp. 779-787. Feb. 1, 2006.

Chinese Office Action issued Jun. 27, 2014 in Chinese Patent Application No. 201180071984.7.

* cited by examiner

Fig. 5

| m/z | TIME | SAMPLE 1 | SAMPLE 2 | SAMPLE 3 | ----- |
|---|---|---|---|---|---|
| 100 | 1.1 | 12 | 0 | 0 | |
| | 1.2 | 3 | 0 | 0 | |
| | 1.3 | 111 | 0 | 20 | |
| | 1.4 | 123 | 0 | 0 | |
| | 1.5 | 31 | 24 | 240 | |
| | 1.6 | 21 | 1 | 174 | |
| | 1.7 | 2 | 211 | 0 | |
| | 1.8 | 34 | 68 | 2 | |
| | ⋮ | ⋮ | ⋮ | ⋮ | |

Fig. 6

| m/z | TIME | SAMPLE 1 | SAMPLE 2 | SAMPLE 3 | ----- |
|---|---|---|---|---|---|
| 100 | 1.5 | 31 | 24 | 240 | |
| | 1.6 | 21 | 1 | 174 | |
| | 1.7 | 2 | 211 | 0 | |
| | 1.8 | 34 | 68 | 2 | |
| | ⋮ | ⋮ | ⋮ | ⋮ | |

Fig. 7

| m/z | TIME | SAMPLE 1 | SAMPLE 2 | SAMPLE 3 | ----- |
|---|---|---|---|---|---|
| 100 | 1.1 | * | * | * | |
| | 1.2 | * | * | * | |
| | 1.3 | * | * | * | |
| | 1.4 | * | * | * | |
| | 1.5 | 31 | 24 | 240 | |
| | 1.6 | 21 | 1 | 174 | |
| | 1.7 | 2 | 211 | 0 | |
| | 1.8 | 34 | 68 | 2 | |
| | ⋮ | ⋮ | ⋮ | ⋮ | |

| m/z | TIME | SAMPLE 1 | SAMPLE 2 | SAMPLE 3 | ----- |
|---|---|---|---|---|---|
| 100 | 1.1 | 12 | 11 * | 11 * | |
| | 1.2 | 3 | 5 * | 5 * | |
| | 1.3 | 111 | 35 * | 20 | |
| | 1.4 | 123 | 41 * | 0 | |
| | 1.5 | 31 | 24 | 240 | |
| | 1.6 | 21 | 1 | 174 | |
| | 1.7 | 2 | 211 | 0 | |
| | 1.8 | 34 | 68 | 2 | |
| | ⋮ | ⋮ | ⋮ | ⋮ | |

METHOD AND SYSTEM FOR PROCESSING ANALYSIS DATA

This is a National Stage of International Application No. PCT/JP2011/064872 filed Jun. 29, 2011, the contents of all of which are incorporated herein by reference in their entirety.

TECHNICAL FIELD

The present invention relates to a method and system for processing data collected by using a chromatographic analyzing system in the broad sense for temporally separating sample components, such as a liquid chromatograph, gas chromatograph or capillary electrophoresis. In particular, it relates to a data processing method and system suitable for processing data collected by an analyzing system in which a technique for one-dimensionally separating components of a sample with time as the separation factor is combined with a detection technique for acquiring, for the sample, signal strengths distinctively separated in one or more dimensions by a separation factor or factors other than time, such as the signal from mass spectrometry, infrared spectrometry, or ultraviolet-visible spectrometry.

BACKGROUND ART

In an analysis such as an LC/MS, GC/MS or CE/MS analysis, in which the liquid chromatography (LC), gas chromatography (GC), capillary electrophoresis (CE) or a similar technique for separating the components of a sample is combined with a mass spectrometry (MS), a large number of components contained in a sample are temporally separated, and a mass spectrometric data is obtained for each component. These techniques make it possible to efficiently analyze a sample in which various kinds of compounds are mixed. Therefore, in recent years, they have been applied to a wide range of fields. However, a problem exists in that the amount of data obtained by the measurement is considerably large. In particular, in the case of performing an evaluation in which the results of analyses of a large number of similar samples are compared, since a large amount of mass spectrometric data is obtained for each sample, the entire amount of data to be processed is so large that a comprehensive analysis is difficult. One conventional technique for dealing with this difficulty is a multivariate analysis, such as a discrimination analysis, principal component analysis or cluster analysis, which are all capable of analyzing a large amount of data in a relatively easy way.

For example, Non-Patent Document 1, Patent Document 1 and other documents disclose a technique in which mass spectrum data obtained for a plurality of samples are processed by a principal component analysis and the results are presented using the charts called the "scores plot" and "loadings plot." Examples of commonly known multipurpose software products for conducting a multivariate analysis of a mass spectrometric data in the previously described manner include SIMCA-P+ produced by Umetrics AB, Sweden, and Pirouette® produced by Infometrix, Inc., USA, which are all easily available. However, for the measurement data to be read and processed by these multivariate analysis software systems, it is necessary to appropriately compile the measurement data to be analyzed (e.g. mass spectrum data or chromatogram data in the case of an LC/MS) into a table format, i.e. a set of numerical data arrayed in a one-dimensional or two-dimensional (rows and columns) form.

Conventionally, in an analysis using an infrared spectrometer (IR) or a nuclear magnetic resonator (NMR), it is common that the data collected from a large number of samples are processed and evaluated by a multivariate analysis. This is due to the fact that, in the case of the IR or NMR, the data obtained by a measurement of a sample is simpler than those obtained by the LC/MS or GC/MS. The result of an analysis by IR or NMR is simple and can be presented by one graph, i.e. a one-dimensional numerical data representing the strength of a signal with respect to a certain kind of physical quantity (i.e. the wavelength for IR or the chemical shift for NMR). Accordingly, when the results of analyses of a plurality of samples must be compared, the entire measurement data can be compiled into a two-dimensional table containing numerical values indicating the signal strengths arranged in two directions, one direction corresponding to the variable showing a sequence number or similar numerical values assigned to each sample and the other direction corresponding to the variable showing the aforementioned physical quantity.

By contrast, the measurement data obtained by an LC/MS, GC/MS or similar system are a collection of signal strengths obtained on two directions corresponding to two independent separation factors, i.e. time and mass-to-charge ratio (m/z). This means that these data themselves are in a two-dimensionally arrayed form. Therefore, when the results of the analyses of a plurality of samples must be compared, it is necessary to convert the two-dimensional array of data into a one-dimensional array and then compile the measurement data of the plurality of samples into one table.

One of the simplest methods for converting the two-dimensional array of data having the dimensions of time and mass-to-charge ratio into a one-dimensional array is to select one specific mass-to-charge ratio from a plurality of mass-to-charge ratios, and another method is to total the signal strengths in the dimension of mass-to-charge ratio. Both methods are intended for virtually fixing the variable corresponding to the dimension of mass-to-charge ratio to one value, which means removing the dimension corresponding to mass-to-charge ratio. Selection of one specific mass-to-charge ratio from a plurality of mass-to-charge ratios corresponds to selection of one extracted ion chromatogram (XIC) from LC/MS (or GC/MS) data. Totaling the signal strengths in the dimension of mass-to-charge ratio throughout the entire range of mass-to-charge ratios corresponds to obtaining a total ion current chromatogram (TIC) from LC/MS data. These methods have the advantages that an uncertainty depending on internal parameters used in the data processing operation for the conversion into a one-dimensionally arrayed form (as will be described later) is reduced, the process is so simple that it puts only a light load on the hardware system, and the processing time is so short that the throughput is high.

However, in the case of the TIC, the information in the dimension of mass-to-charge ratio is entirely lost. In the case of the XIC, although the information of one mass-to-charge ratio is retained, the information on the other mass-to-charge ratios is entirely lost. In any of these cases, it can be said that the obtained result is substantially deficient in the information in the dimension corresponding to mass-to-charge ratio. Such a loss of information in one of the two dimensions leads to the problem that, if the lost information contains some important information that characterizes the difference among the plurality of samples, no appropriate information for evaluating the similarity or difference of those samples can be obtained by multivariate analyses and the samples cannot be correctly compared.

On the other hand, Non-Patent Documents 2 and 3 disclose a technique in which a collection of data obtained by an LC/MS are subjected to a complex data processing operation, including the steps of peak detection and selection, noise removal and strength calculation (e.g. normalization), to remove and/or integrate unnecessary data so as to convert a two-dimensional array of data into a one-dimensional form, after which the measurement data obtained for each of the samples are compiled into a two-dimensional table to be subjected to a principal component analysis. Phenomenome Profiler™, a set of software tools for metabolomics analyses provided by Phenomenome Discoveries Inc., Canada, has the function of compiling a collection of data obtained by an LC/MS capable of $MS^n$ analyses into a two-dimensional table format by performing a data conversion process including the steps of peak detection, smoothing, calibration and so on.

However, such a complex data processing operation puts a heavy load on the hardware system, and therefore, requires high-performance CPUs and large-capacity random access memories. It also lowers the throughput of the process. The previously described data processing operation uses previously set operation parameters, and these parameters can cause a significant difference in the result of the multivariate analysis. The peak detection or similar processing causes the loss of the original information during the process, which may possibly prevent the difference of the samples from being correctly reflected in the results of the multivariate analysis. Due to these reasons, in some cases, it is impossible to correctly compare the samples despite the complicated data processing.

Furthermore, in the LC, GC or similar component separation technique, the point in time at which the same substance is eluted easily changes depending on the measurement conditions (separating conditions) or the state of the system. It is often the case that, although the measurement conditions are exactly the same, the elution time of the same substance varies when the measurement is actually performed a number of times. Such a variation in the elution time prevents correct comparison of the results of measurements of different samples. Therefore, in general, the time axes of the chromatogram data are adjusted so that the elution times of the same substance will be aligned with each other. This time-axis adjustment is achieved by shifting the chromatogram data to be adjusted along the time axis and/or by expanding or contracting the time axis. If a head or tail section of the chromatogram data is shifted as a result of such an adjustment, an instance of missing data occurs.

FIG. 9 is a conceptual diagram schematically illustrating the missing of data. In FIG. 9(a), the two chromatogram data A1 and A2 have their head and tail sections aligned and hence no missing data. In FIG. 9(b), since one of the data is shifted, the head section of A1 does not have a counterpart in A2, while the tail section of A2 does not have a counterpart in A1. In FIG. 9(c), since the time axis of one of the data is expanded and that of the other data is contracted, neither the head nor tail section of A1 has a counterpart in A2. Performing a multivariate analysis or similar processing with such a missing of data intact may possibly result in the incorrect recognition that there is a difference in the head or tail section of the data between the two samples.

BACKGROUND ART DOCUMENT

Patent Document

Patent Document 1: JP-A 2009-25056

Non-Patent Document

Non-Patent Document 1: Jun Yonekubo et al., "Feature of newest Time of Flight Mass Spectrometer LCT Premier™ and Applied for Food Metabolome", *Chromatography*, The Society for Chromatographic Sciences, Vol. 27, No. 2 (2006)

Non-Patent Document 2: Tim P. Sangster et al., "Investigation of analytical variation in metabonomic analysis using liquid chromatography/mass spectrometry", *Rapid Commun. Mass Spectrom.*, Vol. 21, pp. 2965-2970 (2007)

Non-Patent Document 3: Li Xiayan et al., "Advances in separation science applied to metabonomics", *Electrophoresis*, Vol. 29, pp. 3724-3736 (2008)

SUMMARY OF THE INVENTION

Problem to be Solved by the Invention

The present invention has been developed in view of the previously described problem, and its primary objective is to provide a method and system for processing analysis data which can obtain correct information relating to a comparison of samples, i.e. the similarity or difference of samples, while effectively using information included in the measurement data collected for a large number of samples by using an LC/MS, GC/MS or similar analyzing system.

Means for Solving the Problem

The first aspect of the present invention aimed at solving the previously described problem is an analysis data processing method for processing a plurality of chromatogram data obtained for one sample or a plurality of chromatogram data respectively obtained for a plurality of samples, including:

a) a time-axis adjusting step in which time axes of a plurality of target chromatogram data selected for a comparative analysis from the aforementioned plurality of chromatogram data are adjusted so that the appearance times of the same component coincide with each other;

b) a data rectifying step in which, if there is a chromatogram data having an incidence of missing data at a point in time within a head section and a tail section of the plurality of target chromatogram data after the time-axis adjustment, the plurality of target chromatogram data is rectified by deleting data included in a time range where the missing of data has occurred; and c) a table creating step in which the plurality of target chromatogram data that have undergone the data rectifying step on the head section and the tail section are compiled into a two-dimensional table with the data values of each chromatogram data arranged in order of time in a longitudinal or lateral direction and the target chromatogram data arranged in a lateral or longitudinal direction orthogonal to the time-order direction.

The second aspect of the present invention aimed at solving the previously described problem is characterized by including, in place of the data rectifying step in the analysis data processing method according to the first aspect of the present invention, another data rectifying step in which, if there is a chromatogram data having an incidence of missing data at a point in time within a head section and a tail section of the plurality of target chromatogram data after the time-axis adjustment, the plurality of target chromatogram data is rectified by invalidating data included in a time range where the missing of data has occurred.

To "invalidate" means, for example, to add a flag or similar index showing that the data has been invalidated, so as to prevent the numerical value in question from being used for an analysis or other practical processing even if that value is actually present in the table. Accordingly, the "invalidation" is equivalent to deletion of data in the context of an analysis or other practical processing.

The third aspect of the present invention aimed at solving the previously described problem is characterized by including, in place of the data rectifying step in the analysis data processing method according to the first aspect of the present invention, still another data rectifying step in which, if there is a chromatogram data having an incidence of missing data at a point in time within a head section and a tail section of the plurality of target chromatogram data after the time-axis adjustment, the plurality of target chromatogram data is rectified by performing a process of making up data in the data-missing section using the other chromatogram data which are included in the same time range as the data-missing section but have no missing data.

In the data rectifying step of the analysis data processing method according to the third aspect of the present invention, the data in the data-missing section can be made up, for example, by using average values of chromatogram data of the other samples which are being subjected to the comparative analysis and which have no missing data. Such supplementary data are not real data obtained by an analysis, and therefore, should preferably be identified as such by an additional flag or similar index.

An analysis data processing system according to the fourth aspect of the present invention is a system embodying the analysis data processing method according to the first aspect of the present invention. Specifically, it is an analysis data processing system for processing a plurality of chromatogram data obtained for one sample or a plurality of chromatogram data respectively obtained for a plurality of samples, including:

a) a time-axis adjuster for adjusting time axes of a plurality of target chromatogram data selected for a comparative analysis from the aforementioned plurality of chromatogram data so that the appearance times of the same component coincide with each other;

b) a data rectifier for rectifying the plurality of target chromatogram data by deleting, if there is a chromatogram data having an incidence of missing data at a point in time within a head section and a tail section of the plurality of target chromatogram data after the time-axis adjustment, data included in a time range where the missing of data has occurred; and c) a table creator for compiling the plurality of target chromatogram data that have undergone the rectification on the head section and the tail section by the data rectifier, into a two-dimensional table with the data values of each chromatogram data arranged in order of time in a longitudinal or lateral direction and the target chromatogram data arranged in a lateral or longitudinal direction orthogonal to the time-order direction.

An analysis data processing system according to the fifth aspect of the present invention, which embodies the analysis data processing method according to the second aspect of the present invention, is characterized by including, in place of the data rectifier in the analysis data processing system according to the fourth aspect of the present invention, another data rectifier for rectifying the plurality of target chromatogram data by invalidating, if there is a chromatogram data having an incidence of missing data at a point in time within a head section and a tail section of the plurality of target chromatogram data after the time-axis adjustment, data included in a time range where the missing of data has occurred.

An analysis data processing system according to the sixth aspect of the present invention, which embodies the analysis data processing method according to the third aspect of the present invention, is characterized by including, in place of the data rectifier in the analysis data processing system according to the fourth aspect of the present invention, still another data rectifier for rectifying the plurality of target chromatogram data by performing, if there is a chromatogram data having an incidence of missing data at a point in time within a head section and a tail section of the plurality of target chromatogram data after the time-axis adjustment, a process of making up data in a data-missing section by using the other chromatogram data which are included in the same time range as the data-missing section but have no missing data.

In any of the first through sixth aspects of the present invention, the chromatogram data are a set of data obtained with an analyzing system including, for example, a liquid chromatograph, a gas chromatograph, a thin film chromatograph, a capillary electrophoresis or a similar separating device combined with a mass spectrometer, an ultraviolet-visible spectrophotometer, a photodiode array spectrophotometer, an infrared spectrometer, a nuclear magnetic resonance apparatus, a differential refractometer or a similar detector. For example, if the detector is a mass spectrometer, possible choices of the chromatogram include the base peak chromatogram, mass defect chromatogram, isotopic filtered chromatogram and neutral-loss chromatogram in addition to the total ion chromatogram (in which mass-to-charge ratios are disregarded) and extracted ion chromatogram (obtained at a specific mass-to-charge ratio).

In the analysis data processing method according to any of the first through third aspects of the present invention, for example, when chromatogram data respectively obtained from a plurality of samples are to be subjected to a comparative analysis, the time axis of the chromatogram data of each sample is adjusted in the time-axis adjusting step so that the appearance times (retention times) of the same component coincide with each other to the highest possible degree. Since this time-axis adjustment is achieved by shifting, expanding or contracting the time axes, the chromatogram data which have undergone the time-axis adjustment will have a discrepancy in their head and/or tail sections even if the head and tail sections of those chromatogram data were originally aligned. Due to the discrepancy, a portion of the chromatogram data will have data absent, or missing, at a certain point in time within their head and/or tail section. In the data rectifying step, to reduce influences of such a data-missing section, the chromatogram data of all the samples to be subjected to the comparative analysis within a time range where the missing of data has occurred are deleted either actually or virtually through invalidation. Alternatively, instead of deleting data, the data-missing section may be supplemented with data prepared by using other valid data.

In the table creating step, the data values of each of the plurality of target chromatogram data selected for the comparative analysis are arranged, for example, in order of time in a longitudinal direction to create a one-dimensional table, and the plurality of target chromatogram data (i.e. one-dimensional tables) are arranged in a lateral direction orthogonal to the time-order direction to create a two-dimensional table.

A preferable mode of the analysis data processing method according to one of the first through third aspects of the present invention is an analysis data processing method for processing chromatogram data obtained for a plurality of samples collected by using an analyzing system including a chromatographic separator for separating a plurality of components in a sample in a temporal direction and a detector for obtaining a signal strength along a direction corresponding to a parameter different from time for the sample separated into components in the temporal direction by the chromatographic separator, wherein:

the processes according to the time-axis adjusting step and the data rectifying step are performed on a plurality of chromatogram data obtained with the same value of the parameter selected as the target of a comparative analysis of different samples; and the table creating step includes: a one-dimensional table creating step in which a one-dimensional table is created for each sample by gathering chromatogram data which have undergone the data rectifying step on the head section and the tail section into a group with the same value of the aforementioned parameter and joining the created groups in a temporal direction to create a one-dimensional table; and a two-dimensional table creating step in which a two-dimensional table is created by arranging, in a direction orthogonal to the temporal direction, the one-dimensional tables respectively created for different samples in the one-dimensional table creating step.

The "parameter" depends on the kind of detector. Examples of the parameter include the mass-to-charge ratio for mass spectrometers, the wavelength for ultraviolet-visible spectrophotometers or photodiode array spectrophotometers, and the chemical shift for nuclear magnetic resonance apparatuses. According to the previously described, preferable method, for example, a plurality of extracted ion chromatogram data respectively obtained at a plurality of mass-to-charge ratios for one sample are organized into a one-dimensional table, and a plurality of extracted ion chromatogram data corresponding to a plurality of samples are organized into a two-dimensional table.

By the processes described thus far, for example, if the analyzing system is an LC/MS or GC/MS, mass spectrum data and chromatogram data for a plurality of samples are converted into a two-dimensional table format. By inputting the numerical values held in the two-dimensional table into multivariate analysis software and performing a data processing, a comprehensive analysis result reflecting both the information in the temporal direction and the information in the mass-to-charge-ratio direction can be obtained. It is naturally possible to incorporate the functions realized by commonly used multivariate analysis software into the present invention so as to continuously perform the processes from the conversion of data into a two-dimensional table through to the multivariate analysis.

Effect of the Invention

With the method and system for processing analysis data according to the present invention, even if an incidence of missing data in a head or tail section of a plurality of target chromatogram data selected for a comparative analysis occurs as a result of the time-axis adjustment of the chromatogram data, an analytical process for determining the difference or similarity of different samples or for determining the difference or similarity of the results obtained by using different detectors for the same sample will not yield an abnormal result due to the missing of a portion of data. Therefore, a comparative analysis of a plurality of chromatograms can be performed with high accuracy.

BRIEF DESCRIPTION OF THE DRAWINGS

FIG. 5 is a model diagram showing a specific example of the data processing shown in FIG. 3.

FIG. 6 is a model diagram showing a specific example of the data processing shown in FIG. 3.

FIG. 7 is a model diagram showing a specific example of the data processing shown in FIG. 3.

MODE FOR CARRYING OUT THE INVENTION

Figure 1:
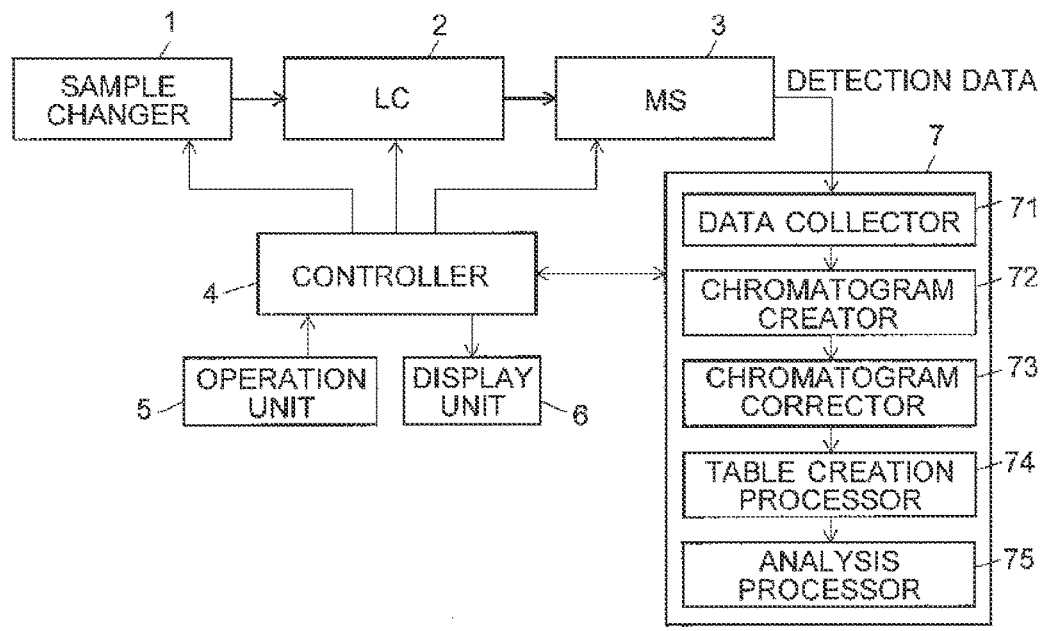
FIG. 1 is a schematic block configuration diagram of one embodiment of an LC-MS analyzer system including an analysis data processing system according to the present invention.

One mode of the analysis data processing method according to the present invention and an analysis data processing system in which the aforementioned method is carried out are hereinafter described, taking as an example an LC-MS analyzer system including the aforementioned analysis data processing system. FIG. 1 is a schematic block diagram showing the configuration of this LC-MS analyzer system.

In FIG. 1, under the control of a controller 4, a sample changer 1 sequentially selects a plurality of prepared samples and introduces it into a liquid chromatograph (LC) unit 2. The LC unit 2, which includes a separation column, receives the sample from the sample changer 1 and introduces it into the column. While passing through this column, the sample is temporally separated into various components, which are then sequentially sent into a mass spectrometer (MS) unit 3.

Though not shown, the MS unit 3 is, for example, an ion trap time-of-flight mass spectrometer (IT-TOFMS) including an atmospheric pressure ionization source (e.g. an electrospray ionization source), an ion trap, a time-of-flight mass analyzer and an ion detector. In this MS unit 3, the sample components in an eluate introduced from the LC unit 2 are ionized. The produced ions are temporarily held in the ion trap. The ions thus held are given a certain amount of kinetic energy in the ion trap and sent into the time-of-flight mass analyzer. While flying in the flight space, the ions are separated according to their mass-to-charge ratios, to be sequentially detected at the ion detector.

The detection signals obtained in the MS unit 3 are sent to a data processor 7, where the signals are converted into digital data and entirely stored in a data collector 71 which includes a data storage. Then, under the command of the controller 4, predetermined data are read from the data collector 71 and sent to a chromatogram creator 72, which creates various chromatograms, such as an extracted ion chromatogram (which is hereinafter abbreviated as "XIC"). Those chromatograms are sent to a chromatogram corrector 73, which performs a time-axis correction and a correction of an incidence of missing data which occurs as a result of the time-axis correction. In a table creation processor 74, mass spectrum data and chromatogram data obtained for a plurality of samples are compiled into one table (a two-dimensional array of data). This table is shown through the controller 4 on a screen of a display unit 6. The same table is also given to an analysis processor 75, in which a differential analysis or other data processing is performed to obtain an analysis result. The result is also displayed through the controller 4 on the screen of the display unit 6.

The controller 4 not only controls the operations of the sample changer 1, the LC unit 2, the MS unit 3 and the data processor 7, but also receives user operations and shows analysis results (e.g. the aforementioned scores plot) through an operation unit 5 and the display unit 6, both units serving as a user interface. Most of the functions of the controller 4 and data processor 7 can be embodied by a personal computer on which a predetermined controlling and processing software program is installed.

In the LC-MS system of the present embodiment, the samples to be analyzed are similar to each other and contain almost the same components. The kinds of components contained are basically known beforehand. Since the mass-to-charge ratio is inherent in each substance and unaffected by the analyzing conditions and other factors, knowing the kinds of components contained means knowing the mass-to-charge ratios to be monitored. Accordingly, the analysis operator, using the operation unit 5, inputs beforehand a plurality of mass-to-charge ratios to be monitored as one item of the measurement conditions, and then enters a command for executing the measurement. In the present example, it is assumed that m/z 100, 101, 120, 130 and so on have been set as the mass-to-charge ratios to be monitored. According to this condition, the MS unit 3, under the control of the controller 4, repeatedly performs a selective ion monitoring (SIM) measurement for m/z 100, 101, 120, 130 and so on.

When the measurement is initiated, the sample changer 1 selects one of the samples in a specified order and sends it into the LC unit 2. The LC unit 2 temporally separates the components in the sample, while the MS unit 3 repeatedly performs the SIM measurement for the mass-to-charge ratios that have been set in the aforementioned manner After the LC/MS measurement for one sample has been completed, the sample changer 1 selects the next sample and sends it into the LC unit 2. The LC unit 2 and the MS unit 3 once again perform the measurements in the previously described manner. Thus, the LC/MS measurement is performed for all the samples. The data collector 71 temporarily holds the thereby obtained data (Step S1).

Figure 2:
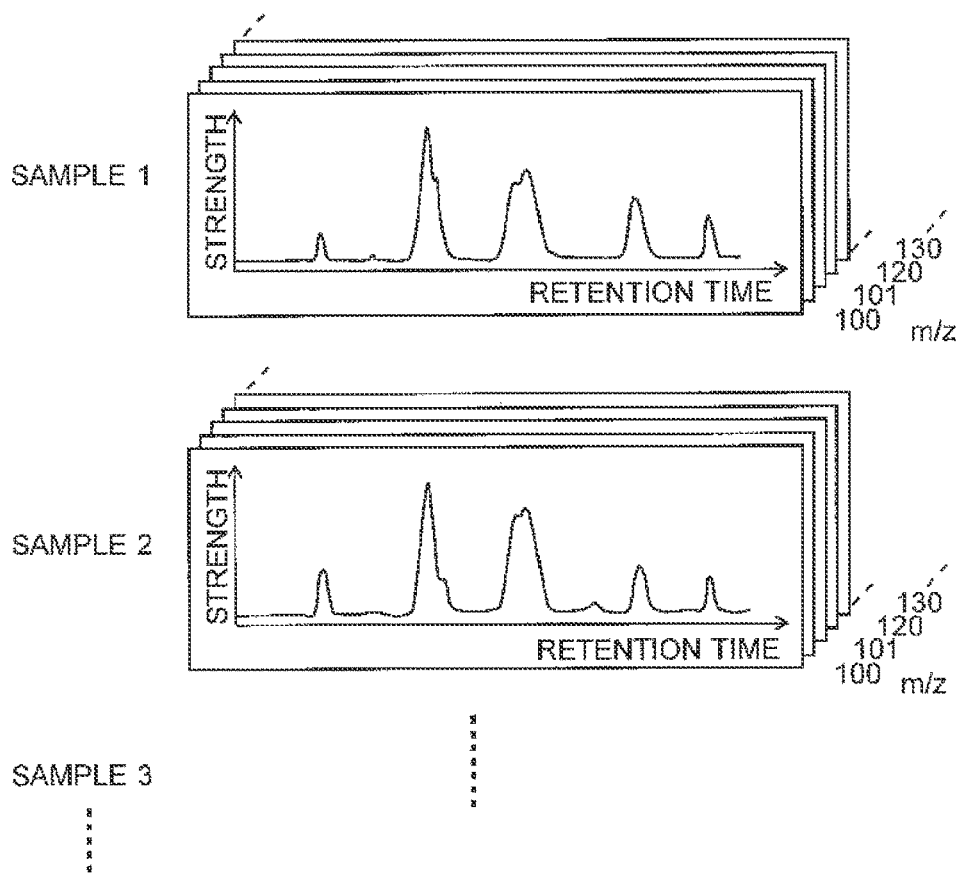
FIG. 2 is a chart illustrating chromatogram data collected in the LC-MS analyzer system of the present embodiment.
Figure 3:
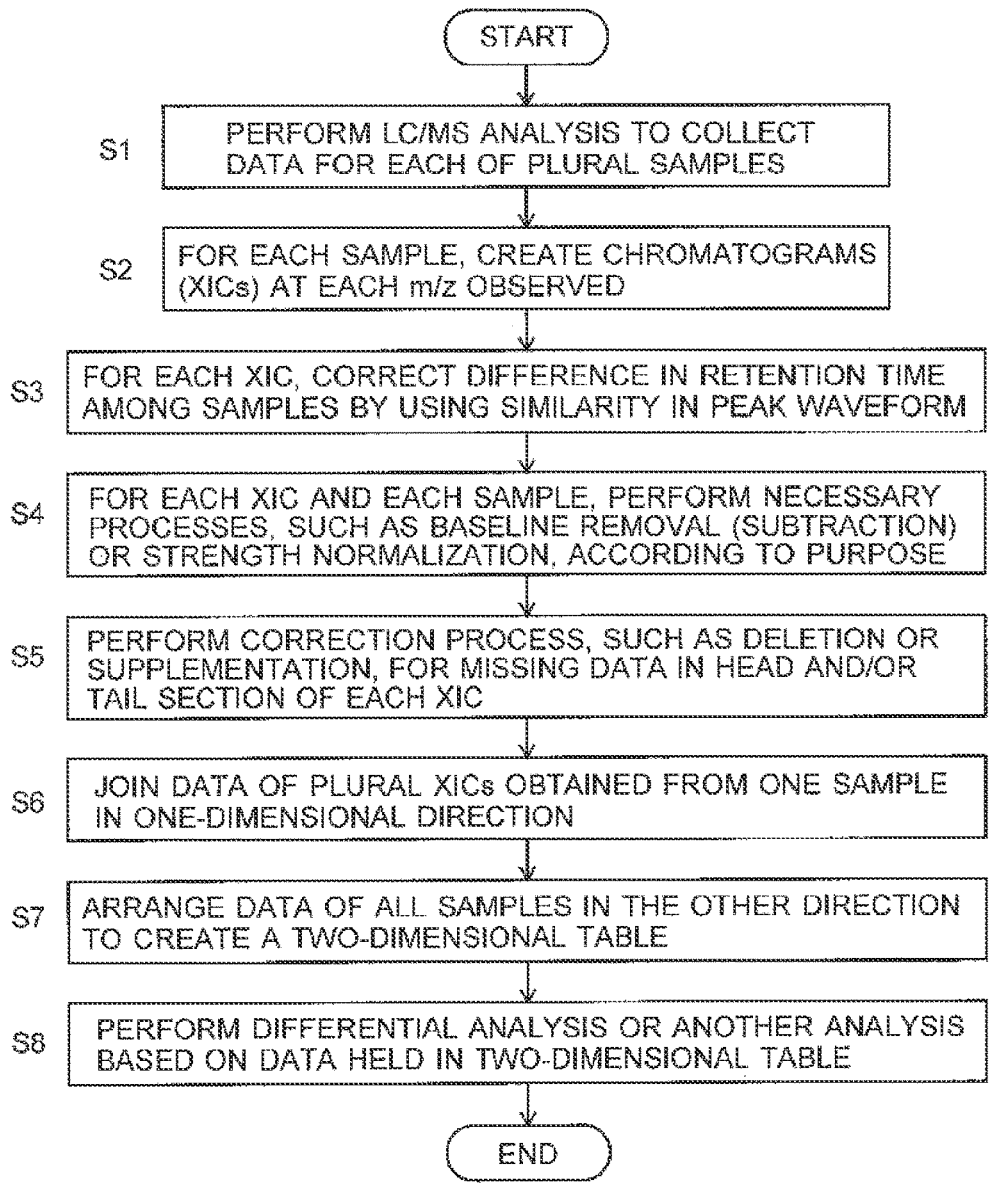
FIG. 3 is a flowchart showing the steps of a data processing characteristic of the LC-MS analyzer system of the present embodiment.

Next, the chromatogram creator 72 creates, for each sample, an XIC for each of the monitored mass-to-charge ratios (Step S2). For example, if the number of monitored mass-to-charge ratios is eight, there will be eight XICs created per one sample (see FIG. 2). The chromatogram corrector 73 compares the peak waveforms of the XICs obtained at the same mass-to-charge ratio of different samples, and based on their similarity, identifies a peak originating from the same component. Then, it calculates the differences in the retention time of the same component and corrects the time axes of the XICs to cancel those differences (Step S3). The differences in the retention time result from the variation in the flow velocity of the mobile phase in the LC unit 2, the variation in the temperature of the column, or the variation of any other factor that affects the component separation characteristics. With the XIC obtained for any one sample as the reference, the time axes of the other XICs are individually shifted, expanded or contracted so as to make the retention times of each component on the chromatograms almost aligned.

Subsequently, the chromatogram corrector 73 performs, for the XICs of each sample, a waveform processing according to the purpose of the measurement or other factors. For example, this processing may include the determination and removal of the baseline of the XICs, or the normalization of the signal strengths on the XICs (Step S4). In the case of normalization, for example, the maximum value, variance or standard deviation of the signal strengths on each XIC can be used as the basis for normalizing each of the signal-strength values.

As a result of the time-axis correction of the XICs, the head and/or tail section of the chromatogram data may possibly be out of alignment, as shown in FIG. 9(b) or 9(c). In such a case, an incidence of missing data occurs, in which one or both of the head and tail sections of a chromatogram data do not have a counterpart section of another chromatogram data in the corresponding time range. Accordingly, the chromatogram corrector 73 performs a process for correcting the missing of data in the head and tail sections of the chromatogram data (Step S5). A specific processing method will be described later.

Subsequently, the data creation processor 74 compiles the time-axis-corrected XIC data of the samples into a two-dimensional table format. Specifically, this process is performed by the following procedure.

Figure 4:
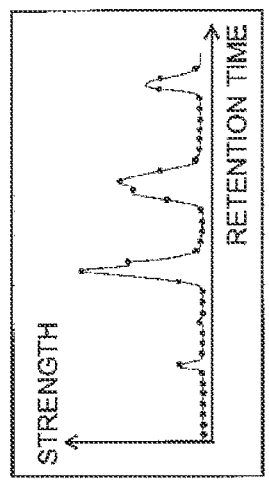
FIG. 4 is a model diagram showing a specific example of the data processing shown in FIG. 3.

The data which constitute an XIC for one mass-to-charge ratio in one sample, as shown in FIG. 4(a), are data each of which indicates the signal-strength value at each point in time (retention time) on the time axis. Taking this into account, a one-dimensional table in which the data values (signal-strength values) are arrayed in a one-dimensional direction with respect to the change in time is created for each XIC in one sample. FIG. 4(b) is one example of the one-dimensional table created for an XIC obtained at m/z 100.

Similar one-dimensional tables are also created for the other mass-to-charge ratios (m/z 101, 120, 130, and so on). These one-dimensional tables are joined in the increasing (or decreasing) order of mass-to-charge ratio in the array direction of the signal-strength values (i.e. in the time-axis direction) held in the tables (Step S6). FIG. 4(c) is one example created by joining one-dimensional tables for different mass-to-charge ratios in Sample 1. In the one-dimensional direction of the obtained table (the longitudinal direction in FIG. 4(c)), the signal-strength values are not grouped by the retention time, which is a type of information that can be affected by the measurement conditions or other factors, but by the mass-to-charge ratio, which is a type of information inherent in the substance.

Similarly, a one-dimensional table in which signal-strength values constituting a plurality of XICs are arrayed in a one-dimensional direction is created for each of the samples. Then, the one-dimensional tables created for all the samples are arranged in the other dimensional direction in order of the number assigned to each sample, so as to combine them into a two-dimensional table format as shown in FIG. 4(d) (Step S7). That is to say, in the two-dimensional table shown in FIG. 4(d), each longitudinal column holds signal-strength data of all the XICs in one sample. In each column, the signal-strength values for the same mass-to-charge ratio are adjacently held in a packed form. On the other hand, each lateral row holds signal-strength data of all the samples obtained at one mass-to-charge ratio and at one point in time.

The process of correcting the missing of data performed in Step S5 is hereinafter specifically described. First, suppose that the table creating process of Steps S6 and S7 has been performed without the process of correcting the missing of data. The obtained two-dimensional table will be as shown in FIG. 5. In FIG. 5, Sample 1 has some data (signal-strength values) within a range of retention time from 1.1 to 1.4. On the other hand, the data of Sample 2 within the range of retention time from 1.1 to 1.4 are missing, and the "0" data are put in this range for convenience. Similarly, the data of Sample 3 within the range of retention time from 1.1 to 1.2 are missing, and the "0" data are put in this range for convenience. The areas surrounded by the thick dotted lines in FIG. 5 correspond to the data-missing sections. These sections are located at the head of the chromatogram data in the present example. The missing of data can similarly occur in the tail section.

Accordingly, in Step S5, one of the following three processes is performed to correct the data-missing sections so that they will not affect the result of a differential analysis (which will be described later) or other analyses.

(1) The data within a time range in which the missing of data has occurred are deleted from the chromatogram data of all the samples.

In the example of FIG. 5, since the data of Sample 2 within the range of retention time from 1.1 to 1.4 are missing, the data within the range of retention time from 1.1 to 1.4 are deleted from the chromatogram data of all the samples. As a result, the head of the data moves from 1.1 to 1.5 in retention time. FIG. 6 shows a two-dimensional table created for the XICs on which the aforementioned missing-data correcting process (1) has been performed in Step S5. As can be seen in FIG. 6, the two-dimensional table retains no sign of the fact that there were data-missing sections.

(2) The data within a time range in which the missing of data has occurred are invalidated in the chromatogram data of all the samples. More specifically, although the data are not actually deleted, they are made unavailable for an automatic analysis or manual analysis by inserting, instead of a normal numerical value, a numerical value which cannot practically occur or a special symbol, or by adding a flag which indicates that the data is invalid.

In the example of FIG. 5, since the data of Sample 2 within the range of retention time from 1.1 to 1.4 are missing, the data within the range of retention time from 1.1 to 1.4 are replaced by the special symbol "*" on the chromatogram data of all the samples, as shown in FIG. 7. As can be seen in FIG. 7, in the present case, it is possible to recognize from the two-dimensional table that there were data-missing sections.

(3) The data in the missing sections (those surrounded by the thick dotted lines in FIG. 5) are replaced by data derived from non-missing data by calculation or other operations. For example, an average of the data of the other samples at each retention time concerned is calculated, and the "0" values in the data-missing sections are replaced by the corresponding average-value data.

Figures 8, 9:
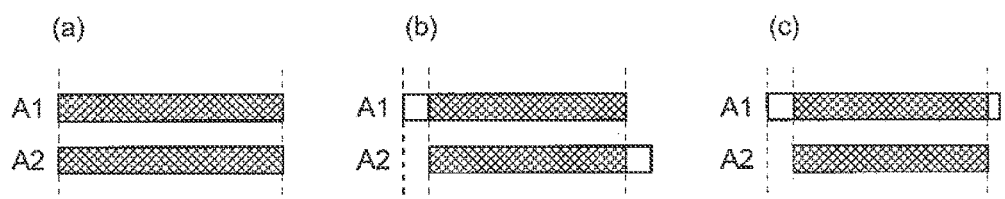
FIG. 8 is a model diagram showing a specific example of the data processing shown in FIG. 3.
FIG. 9 is a conceptual diagram schematically illustrating the missing of data which occurs as a result of a time-axis adjustment of chromatograms.

In the example of FIG. 5, since the data of Sample 2 within the range of retention time from 1.1 to 1.4 are missing, average values are calculated from the chromatogram data of the other samples which have no data missing within the range of retention time from 1.1 to 1.4, and the missing data are replaced by the average values, as shown in FIG. 8. It is preferable to add a specific flag to the calculated data so as to make them distinguishable from original data. In FIG. 8, the special symbol "*" is added to the data in question.

When the signal-strength data compiled into the previously described two-dimensional table format by the table creation processor 74 are sent to the analysis processor 75, the analysis processor 75 performs a predetermined type of differential analysis or multivariate analysis to obtain a result demonstrating the similarity or difference of the samples, and shows the result on the display unit 6 (Step S8). In the case where the analysis processor 75 performs a principal component analysis, the scores and loadings are computed for each sample on the basis of the read signal-strength data, and the respective dispersion diagrams are created and displayed. With these diagrams, the analysis operator can evaluate the similarity or difference of a plurality of samples.

In the case where a differential analysis is performed by the analysis processor 75, the analysis makes use of the difference in the data obtained at the same retention time for different samples. In the examples of FIGS. 6 and 7, the missing of data does not affect the analysis result since the time range in which the missing of data has occurred is excluded from the differential analysis. In the example of FIG. 8, although the time range in which the missing of data has occurred is also included in the differential analysis, the influence on the analysis result will be limited since the missing data are not zero data but have some values which are close to the corresponding data of the other samples.

In the previously described embodiment, the chromatogram data shown in FIG. 4(b) are signal-strength data of an XIC for one mass-to-charge ratio, and a one-dimensional table as shown in FIG. 4(c) is created by using signal-strength data of XICs for a number of mass-to-charge ratios. However, a portion or all of those chromatograms may be replaced by another type of chromatogram different from the XIC.

For example, it is possible to use a differential chromatogram obtained by computing the difference between the XICs of a plurality of mass-to-charge ratios, or an addition chromatogram obtained by adding the XICs of a plurality of mass-to-charge ratios or by adding all the XICs over a predetermined range of mass-to-charge ratios. For example, in the case of FIG. 4(c), the data showing the two XICs obtained at m/z 100 and m/z 101 may be replaced with the data showing one chromatogram obtained by adding the two XICs, i.e. a chromatogram corresponding to m/z=100+101. Such a conversion causes no loss of information in the dimension of mass-to-charge ratio.

In addition to the TIC and XIC, which are the most common chromatograms created by mass spectrometers, there are various forms of chromatograms that can be created. Data which constitute such chromatograms may also be included in the one-dimensional table shown in FIG. 4(c). Examples of such chromatograms include a base peak chromatogram, which is a collection of peaks at which the amount of ions is largest, a mass defect chromatogram, an isotopic filtered chromatogram, and a neutral-loss chromatogram. Naturally, it should be understood that some of these chromatograms are based on the data collected by a mass spectrometry of a precursor ion produced by dissociating ions in the MS unit 3.

The previously described embodiment is an application of the present invention to an LC-MS analyzer system. It is evident that a GC or CE system, which is similarly capable of separating components in the temporal direction, can be used in place of the LC.

It is also evident that various types of analyzing devices other than the mass spectrometer can be used as the detector for acquiring measurement data for samples. For example, in the case where an ultraviolet-visible spectrophotometer or photodiode array detector is used as the detector, it is possible to measure the temporal change of the signal strength for each of a plurality of wavelengths. Accordingly, a chromatogram can be created for each wavelength, and chromatogram data of a plurality of wavelengths obtained for a plurality of samples can be combined into a two-dimensional table by a method similar to the previously described one.

In the previously described system, a plurality of chromatogram data obtained for a plurality of samples are arranged in the lateral direction of the table so as to compare chromatogram data of different samples. It is also possible to use the present invention to compare a plurality of chromatograms each of which was obtained from the same sample by using a different detector. Specifically, for example, it is possible to compare a TIC obtained with a mass spectrometer for one sample and a plurality of chromatograms obtained at different wavelengths with an ultraviolet-visible spectrophotometer for the same sample by using a two-dimensional table created by laterally arranging a plurality of one-dimensional tables each of which holds one of those chromatogram data in the form of an array. Thus, users can arbitrarily select the kinds of chromatograms to be compared. Whatever kinds of chromatograms are selected, the influence of the missing of data resulting from the time-axis adjustment is cancelled by the present invention and the chromatograms can be correctly compared.

It should be noted that the previously described embodiment is a mere example of the present invention, and any change, modification or addition appropriately made within the spirit of the present invention will naturally fall within the scope of claims of the present patent application.

EXPLANATION OF NUMERALS

1 . . . Sample Changer
2 . . . Liquid Chromatograph (LC) Unit
3 . . . Mass Spectrometer (MS) Unit
4 . . . Controller
5 . . . Operation Unit
6 . . . Display Unit
7 . . . Data Processor
71 . . . Data Collector
72 . . . Chromatogram Creator
73 . . . Chromatogram Corrector
74 . . . Table Creation Processor
75 . . . Analysis Processor

The invention claimed is:
1. An analysis method, comprising:
a mass analysis step in which a plurality of chromatogram data are obtained for one sample or a plurality of chromatogram data are respectively obtained for a plurality of samples;
a time-axis adjusting step in which time axes of a plurality of target chromatogram data selected for a comparative analysis from the aforementioned plurality of chromatogram data are adjusted so that appearance times of the same component coincide with each other;
a data rectifying step in which, if there is a chromatogram data having an incidence of missing data at a point in time within a head section and a tail section of the plurality of target chromatogram data after the time-axis adjustment, the plurality of target chromatogram data is rectified by deleting data included in a time range where the missing of data has occurred;
a table creating step in which the plurality of target chromatogram data that have undergone the data rectifying step on the head section and the tail section are compiled into a two-dimensional table with data values of each chromatogram data arranged in order of time in a longitudinal or lateral direction and the target chromatogram data arranged in a lateral or longitudinal direction orthogonal to the time-order direction; and
a sample analysis step in which a predetermined type of analysis is performed on the two-dimensional table with the data values, and the results of the analysis are output.

2. An analysis method, comprising:
a mass analysis step in which a plurality of chromatogram data are obtained for one sample or a plurality of chromatogram data are respectively obtained for a plurality of samples;
a time-axis adjusting step in which time axes of a plurality of target chromatogram data selected for a comparative analysis from the aforementioned plurality of chromatogram data are adjusted so that appearance times of the same component coincide with each other;
a data rectifying step in which, if there is a chromatogram data having an incidence of missing data at a point in time within a head section and a tail section of the plurality of target chromatogram data is rectified by invalidating data after the time-axis adjustment, the plurality of target chromatogram data included in a time range where the missing of data has occurred;
a table creating step in which the plurality of target chromatogram data that have undergone the data rectifying step on the head section and the tail section in the data rectifying step are compiled into a two-dimensional table with data values of each chromatogram data arranged in order of time in a longitudinal or lateral direction and the target chromatogram data arranged in a lateral or longitudinal direction orthogonal to the time-order direction; and
a sample analysis step in which a predetermined type of analysis is performed on the two-dimensional table with the data values, and the results of the analysis are output.

3. An analysis method, comprising:
a mass analysis step in which a plurality of chromatogram data are obtained for one sample or a plurality of chromatogram data are respectively obtained for a plurality of samples;
a time-axis adjusting step in which time axes of a plurality of target chromatogram data selected for a comparative analysis from the aforementioned plurality of chromatogram data are adjusted so that appearance times of the same component coincide with each other;
a data rectifying step in which, if there is a chromatogram data having an incidence of missing data at a point in time within a head section and a tail section of the plurality of target chromatogram data after the time-axis adjustment, the plurality of target chromatogram data is rectified by performing a process of making up data in the data-missing section using other chromatogram data which are included in a same time range as the data-missing section but have no missing data;

a table creating step in which the plurality of target chromatogram data that have undergone the data rectifying step on the head section and the tail section in the data rectifying step are compiled into a two-dimensional table with data values of each chromatogram data arranged in order of time in a longitudinal or lateral direction and the target chromatogram data arranged in a lateral or longitudinal direction orthogonal to the time-order direction; and a sample analysis step in which a predetermined type of analysis is performed on the two-dimensional table with the data values, and the results of the analysis are output.

4. The analysis method according to claim 1, in the chromatogram data is obtained for a plurality of samples collected by using an analyzing system including a chromatographic separator for separating a plurality of components in a sample in a temporal direction and a detector for obtaining a signal strength along a direction corresponding to a parameter different from time for the sample separated into components in the temporal direction by the chromatographic separator, wherein:

the processes according to the time-axis adjusting step and the data rectifying step are performed on a plurality of chromatogram data obtained with a same value of the parameter selected as a target of a comparative analysis of different samples; and the table creating step includes: a one-dimensional table creating step in which a one-dimensional table is created for each sample by gathering chromatogram data which have undergone the data rectifying step on the head section and the tail section in the data rectifying step into a group with the same value of the aforementioned parameter and joining the created groups in a temporal direction to create a one-dimensional table; and a two-dimensional table creating step in which a two-dimensional table is created by arranging, in a direction orthogonal to the temporal direction, the one-dimensional tables respectively created for different samples in the one-dimensional table creating step.

5. The analysis method according to claim 4, wherein:
the detector is a mass spectrometer, and the parameter is a mass-to-charge ratio.

6. An analysis system, comprising:
a mass analyzer that obtains a plurality of chromatogram data for one sample or a plurality of chromatogram data respectively for a plurality of samples;
a data processor, including
 a) a time-axis adjuster for adjusting time axes of a plurality of target chromatogram data selected for a comparative analysis from the aforementioned plurality of chromatogram data so that appearance times of the same component coincide with each other;
 b) a data rectifier for rectifying the plurality of target chromatogram data by deleting, if there is a chromatogram data having an incidence of missing data at a point in time within a head section and a tail section of the plurality of target chromatogram data after the time-axis adjustment, data included in a time range where the missing of data has occurred;
 c) a table creator for compiling the plurality of target chromatogram data that have undergone the rectification on the head section and the tail section by the data rectifier, into a two-dimensional table with data values of each chromatogram data arranged in order of time in a longitudinal or lateral direction and the target chromatogram data arranged in a lateral or longitudinal direction orthogonal to the time-order direction; and
 d) an analysis processor for performing a predetermined type of analysis on the two-dimensional table with the data values; and
an output that outputs the results of the analysis.

7. An analysis system, comprising:
a mass analyzer that obtains a plurality of chromatogram data for one sample or a plurality of chromatogram data respectively for a plurality of samples;
a data processor, including
 a) a time-axis adjuster for adjusting time axes of a plurality of target chromatogram data selected for a comparative analysis from the aforementioned plurality of chromatogram data so that appearance times of the same component coincide with each other;
 b) a data rectifier for rectifying the plurality of target chromatogram data by invalidating, if there is a chromatogram data having an incidence of missing data at a point in time within a head section and a tail section of the plurality of target chromatogram data after the time-axis adjustment, data included in a time range where the missing of data has occurred;
 c) a table creator for compiling the plurality of target chromatogram data that have undergone the rectification on the head section and the tail section by the data rectifier, into a two-dimensional table with data values of each chromatogram data arranged in order of time in a longitudinal or lateral direction and the target chromatogram data arranged in a lateral or longitudinal direction orthogonal to the time-order direction; and
 d) an analysis processor for performing a predetermined type of analysis on the two-dimensional table with the data values; and
an output that outputs the results of the analysis.

8. An analysis system, comprising:
a mass analyzer that obtains a plurality of chromatogram data for one sample or a plurality of chromatogram data respectively for a plurality of samples;
a data processor, including
 a) a time-axis adjuster for adjusting time axes of a plurality of target chromatogram data selected for a comparative analysis from the aforementioned plurality of chromatogram data so that appearance times of the same component coincide with each other;
 b) a data rectifier for rectifying the plurality of target chromatogram data by performing, if there is a chromatogram data having an incidence of missing data at a point in time within a head section and a tail section of the plurality of target chromatogram data after the time-axis adjustment, a process of making up data in a data-missing section by using other chromatogram data which are included in a same time range as the data-missing section but have no missing data; and
 c) a table creator for compiling the plurality of target chromatogram data that have undergone the rectification on the head section and the tail section by the data rectifier, into a two-dimensional table with data values of each chromatogram data arranged in order of time in a longitudinal or lateral direction and the target chromatogram data arranged in a lateral or longitudinal direction orthogonal to the time-order direction;

d) an analysis processor for performing a predetermined type of analysis on the two-dimensional table with the data values; and an output that outputs the results of the analysis.

9. The analysis method according to claim 2, in which the chromatogram data obtained for a plurality of samples is collected by using an analyzing system including a chromatographic separator for separating a plurality of components in a sample in a temporal direction and a detector for obtaining a signal strength along a direction corresponding to a parameter different from time for the sample separated into components in the temporal direction by the chromatographic separator, wherein:

the processes according to the time-axis adjusting step and the data rectifying step are performed on a plurality of chromatogram data obtained with a same value of the parameter selected as a target of a comparative analysis of different samples; and the table creating step includes: a one-dimensional table creating step in which a one-dimensional table is created for each sample by gathering chromatogram data which have undergone the data rectifying step on the head section and the tail section in the data rectifying step into a group with the same value of the aforementioned parameter and joining the created groups in a temporal direction to create a one-dimensional table; and a two-dimensional table creating step in which a two-dimensional table is created by arranging, in a direction orthogonal to the temporal direction, the one-dimensional tables respectively created for different samples in the one-dimensional table creating step.

10. The analysis data processing method according to claim 9, wherein:

the detector is a mass spectrometer, and the parameter is a mass-to-charge ratio.

11. The analysis data processing method according to claim 3, in which the chromatogram data is obtained for a plurality of samples collected by using an analyzing system including a chromatographic separator for separating a plurality of components in a sample in a temporal direction and a detector for obtaining a signal strength along a direction corresponding to a parameter different from time for the sample separated into components in the temporal direction by the chromatographic separator, wherein:

the processes according to the time-axis adjusting step and the data rectifying step are performed on a plurality of chromatogram data obtained with a same value of the parameter selected as a target of a comparative analysis of different samples; and the table creating step includes: a one-dimensional table creating step in which a one-dimensional table is created for each sample by gathering chromatogram data which have undergone the data rectifying step on the head section and the tail section in the data rectifying step into a group with the same value of the aforementioned parameter and joining the created groups in a temporal direction to create a one-dimensional table; and a two-dimensional table creating step in which a two-dimensional table is created by arranging, in a direction orthogonal to the temporal direction, the one-dimensional tables respectively created for different samples in the one-dimensional table creating step.

12. The analysis data processing method according to claim 11, wherein:

the detector is a mass spectrometer, and the parameter is a mass-to-charge ratio.

\* \* \* \* \*